(12) United States Patent
Norcross, Jr.

(10) Patent No.: US 8,869,600 B2
(45) Date of Patent: Oct. 28, 2014

(54) FALLING-PISTON VISCOMETER AND METHODS FOR USE THEREOF

(75) Inventor: Robert A. Norcross, Jr., Newton, MA (US)

(73) Assignee: Norcross Corporation, Newton, MA (US)

( * ) Notice: Subject to any disclaimer, the term of this patent is extended or adjusted under 35 U.S.C. 154(b) by 307 days.

(21) Appl. No.: 13/336,631

(22) Filed: Dec. 23, 2011

(65) Prior Publication Data
US 2013/0160528 A1  Jun. 27, 2013

(51) Int. Cl.
*G01N 11/00* (2006.01)

(52) U.S. Cl.
USPC ........................................ 73/54.15; 73/54.01

(58) Field of Classification Search
CPC ....................................................... G01N 11/12
USPC ............ 73/54.01, 54.02, 54.03, 54.11, 54.13, 73/54.14, 54.15
See application file for complete search history.

(56) References Cited

U.S. PATENT DOCUMENTS

| | | | |
|---|---|---|---|
| 2,491,389 A | 12/1949 | Norcross | |
| 2,526,832 A * | 10/1950 | Smith | 73/54.11 |
| 2,630,819 A | 3/1953 | Norcross | |
| 3,304,765 A | 2/1967 | Norcross | |
| 3,371,522 A * | 3/1968 | Norcross | 73/54.15 |
| 3,512,396 A * | 5/1970 | Okamoto | 73/54.21 |
| 3,677,070 A * | 7/1972 | Norcross | 73/54.21 |
| 3,686,931 A * | 8/1972 | Norcross | 73/54.16 |
| 3,717,026 A | 2/1973 | Ito | |
| 3,782,174 A | 1/1974 | Varadi et al. | |
| 4,154,094 A | 5/1979 | Norcross | |
| 4,627,272 A * | 12/1986 | Wright | 73/54.23 |
| 4,864,849 A | 9/1989 | Wright | |
| 5,327,778 A * | 7/1994 | Park | 73/54.21 |
| 5,388,447 A | 2/1995 | Fitch et al. | |
| 5,569,843 A * | 10/1996 | Poissant | 73/54.07 |
| 5,677,481 A | 10/1997 | Brown et al. | |
| 5,959,196 A * | 9/1999 | Norcross, Jr. | 73/54.18 |
| 7,890,275 B2 * | 2/2011 | Takahashi et al. | 702/50 |
| 8,555,706 B2 * | 10/2013 | Kawamura et al. | 73/54.15 |

FOREIGN PATENT DOCUMENTS

| | | |
|---|---|---|
| JP | 06-082545 | 11/1994 |
| JP | 2000-321192 A | 11/2000 |

OTHER PUBLICATIONS

International Search Report for International Application No. PCT/US2012/069717 dated Apr. 8, 2013.
Written Opinion for International Application No. PCT/US2012/069717 dated Apr. 8, 2013.

* cited by examiner

*Primary Examiner* — Randy W Gibson
*Assistant Examiner* — Natalie Huls
(74) *Attorney, Agent, or Firm* — Edwards Wildman Palmer LLP; Stephen D. LeBarron

(57) ABSTRACT

A falling piston viscometer which includes a measuring bushing and a piston configured to be slidably receivable inside the measuring bushing is provided herein. More specifically, the circumferential edge of first section of the piston in the described falling piston assembly is modified to allow for decreased friction and sensitivity. A lifting mechanism, in communication with the piston and piston rod, raises the piston to an upper piston position within the measuring bushing, upon instruction from a controller. Upon the piston being lifted, fluid is drawn into the measuring bushing. The controller is configured to maintain the piston in a raised position for a pre-programmed time, after which, the controller allows the piston to fall, by the force of gravity.

18 Claims, 7 Drawing Sheets

FALLING-PISTON VISCOMETER AND METHODS FOR USE THEREOF

FIELD OF THE INVENTION

The present invention is directed to a falling piston for a viscometer and a method for using the same. Such inventions are applicable, for example, to industrial processes such as printing.

BACKGROUND

Viscosity control is essential in many of today's manufacturing and printing processes. Viscosity is the measure of the resistance of a fluid to deformation by either shear stress or extensional stress, but is commonly perceived as the "thickness" or resistance to flow of a fluid. Viscosity can be an important quality of a finished product (e.g., a lubricant, paint, or ink) or can affect a finished product (e.g., printed material). Perhaps more importantly, an inappropriate viscosity can adversely affect modern industrial equipment. For example, if the viscosity of printing ink falls outside of an acceptable viscosity ranges, not only is print quality affected, but the printing press can also become fouled. In addition, excess fluid, especially in the case of ink, is applied is the viscosity is not correct, thus wasting natural resources required to make the ink.

Conventional falling piston viscometers measure viscosity of a fluid based on the time required for a piston to fall a distance in a bushing containing the fluid. Such conventional falling piston viscometers require that the depth of the liquid in a measuring bushing be at least 5 inches in order to get an accurate reading. This means that in many smaller applications, as the fluid is consumed or used, the level of the liquid in the tank (not shown) falls below a point where the viscometer can measure the fluid's viscosity.

Also, due to the geometric symmetry of the conventional falling piston viscometer, the piston rod must be very straight/linear in order for the viscometer to measure lower viscosities accurately. In most cases, if the rod is even slightly bent and/or has a diameter outside of a defined tolerance, the viscometer will not function properly. Thus, it can be very costly and time consuming to produce piston rods sufficiently straight due to the skill level of certain manufactures and the materials that are required.

Accordingly, there is a need for viscometers that can be incorporate less-expensive piston rods (which may or may not be sufficiently straight).

Additionally, the conventional viscosity systems are often overly-sensitive, sometimes showing minor changes that can cause unnecessary concern to a user. Thus, it would also be advantageous to produce a device that also has decreased sensitivity.

SUMMARY OF THE INVENTION

The present invention relates to a falling piston viscometer. More specifically, the viscometer includes a measuring bushing and a piston slidably receivable inside the measuring bushing. More specifically, in the present invention the circumferential edge of a first section of the piston is modified, e.g., rounded. A lifting mechanism, in communication with the piston and piston rod, is configured to raise the piston to an upper piston position within the measuring bushing, upon instruction from a remote controller. Upon being lifted, fluid is drawn into the measuring bushing. The remote controller is configured to maintain the piston in a raised position for a pre-programmed time, after which, the remote controller allows the piston to fall, by the force of gravity. A switch mounted proximate to the piston senses when the piston reaches a lower piston position. In particular, the time taken for the piston to travel from the upper piston position to the lower piston position is a direct function of the viscosity of fluid received in the measuring bushing.

By rounding the circumferential edge of the first section of the piston, the present invention is able to provide suitably accurate viscosity measurement even if the piston is not perfectly aligned with the measuring bushing. For example, the piston is able to deviate from a central axis of the measuring bushing at an angle between about 0.1 degrees and about 20 degrees.

In another aspect of the exemplary embodiment of the present invention, the measuring bushing, having an internal depth of about ¾ inch, is formed in a plate and is configured to receive the piston. The plate may be designed as a 1 inch thick plate, made of metal, plastic or a combination thereof. The piston is configured to be raised to an upper piston position which is about ½ inch from the bottom of the measuring bushing in order to draw fluid into the measuring bushing.

In some embodiments of the present invention, an external controller may be configured to measure time taken for the piston to fall from the upper piston position to the lower piston position. Based on this measurement, the controller is able to determine the viscosity of the fluid in the measuring bushing. The fluid may be any number of fluids, however, the illustrative embodiment is discussed herein using either water-based fluids and solvent-based fluids, for example, ink. However, alternative types of fluids may also be readily measured as well.

Furthermore, in some embodiments of the present invention, the piston rod may include a magnet which is utilized in conjunction with a magnetic switch to detect the position of the piston in the measuring bushing. In this embodiment, the magnet in the piston rod operates the magnetic switch to measure the time it takes for the piston to fall, due to the effects of gravity, through the fluid which is received in the measuring bushing. In other embodiments of the present invention, the switch may also be a mechanical switch which is utilized to detect the position of the piston in the measuring bushing.

Also since the piston, piston rod and the measuring bushing of the illustrative embodiment of the present invention need not be perfectly aligned like those in the prior art, these elements may be made of metal, plastic or combination thereof. Thus, the costs associated with the manufacture of these elements can be greatly reduced.

In another aspect of the present invention method for measuring the viscosity of a fluid using a measuring bushing in a viscometer is provided. In particular, illustrative method raises a piston to an upper piston position in the measuring bushing from a position in the bottom of the measuring bushing. In particular the circumferential edge of a first section of the piston is modified so as to allow for a viscosity measurement even when the piston and piston rod are not perfectly aligned. Fluid is then received in the measuring bushing and the piston is allowed to fall back to the bottom of the measuring bushing. As the piston falls, its position is sensed, by a switch, until the piston reaches a lower piston position. A remote controller then correlates the time taken for the piston to travel from the upper piston position to the lower piston position with a viscosity of fluid received in the measuring bushing.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DETAILED DESCRIPTION OF THE INVENTION

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The present invention relates to a falling piston for viscometer which is designed to allow for a more cost efficient means for producing and manufacturing conventional falling piston viscometers. In particular, the present invention provides a falling piston assembly which does not require that a piston rod be perfectly aligned with the measuring bushing, and thus can be made from cheaper materials such as plastic or less expensive metals. Furthermore, the present invention allows for decreased sensitivity in comparison to prior viscometers.

The present invention relates to a falling piston viscometer. More specifically, the viscometer includes a measuring bushing and a piston slidably receivable inside the measuring bushing. More specifically, in the present invention the circumferential edges of a first section of the piston are modified to form a modified circumferential edge. The modified circumferential edge may be, for example, rounded, beveled, etc, so as to allow the piston to be angulated from the axis of piston without sacrificing accuracy in the viscometer's readings. A lifting mechanism, in communication with the piston and piston rod, is configured to raise the piston to an upper piston position within the measuring bushing, upon instruction from a remote controller. Upon being lifted, fluid is drawn into space W, FIG. 3, of the measuring bushing. The remote controller is configured to maintain the piston in a raised position for a pre-programmed time, after which, the remote controller allows the piston to fall, by the force of gravity. A switch mounted proximate to the piston senses when the piston reaches a lower piston position. In particular, the time taken for the piston to travel from the upper piston position to the lower piston position is a direct function of the viscosity of fluid received in the measuring bushing.

Figure 1:
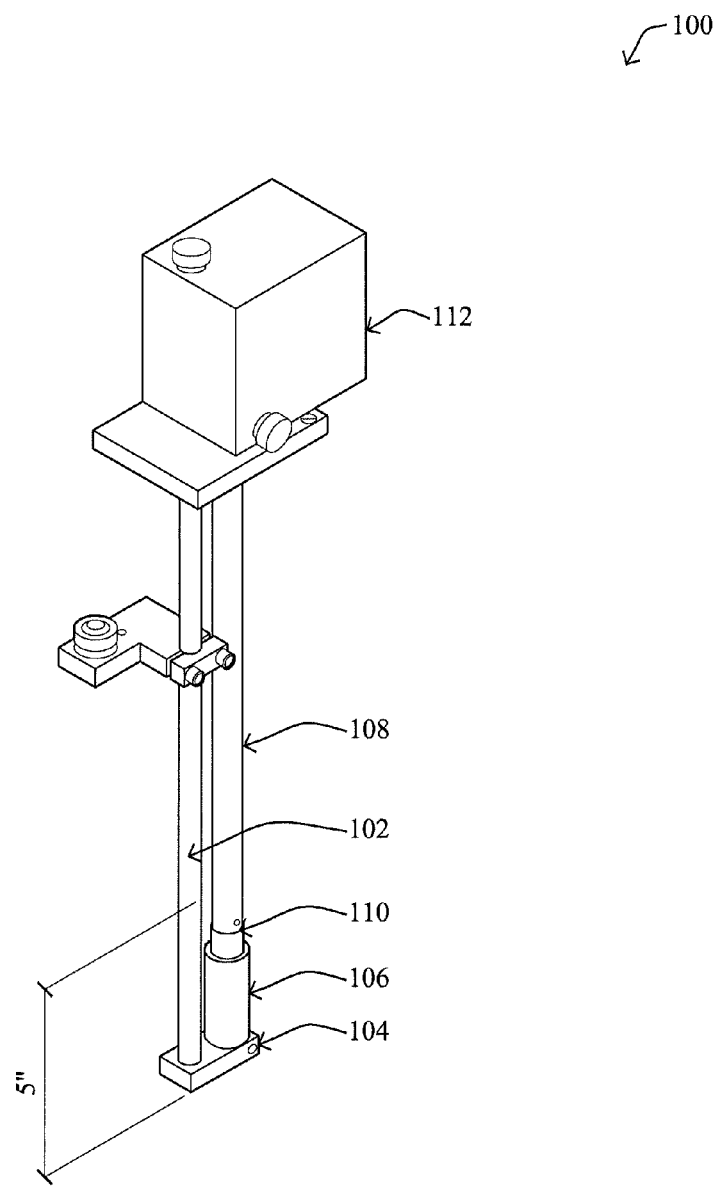
FIG. 1 is a schematic diagram of a viscosity sensing system.

International Publication No. WO 2010/111366 teaches a viscosity control system which includes a viscometer to measure the viscosity of a fluid in a tank. This viscosity control system 100 illustrated in FIG. 1 includes a falling piston viscometer. The falling piston viscometer includes a supporting shaft 102 connected to a bracket or plate 104 for supporting a measuring bushing 106. A lifter cylinder (not shown, but is located under cover 112) is periodically lifted via a hydraulic mechanical means, thereby lifting a piston rod 108 and a piston 110 to allow fluid to be drawn into the measuring bushing 106. After the piston 110 is raised to a specific position (about 1¼ to 1½ inches, cumulatively about 4½ inches, i.e., including the plate 104, the measuring bushing 106 and the piston 110 at its raised position), the measuring bushing 106 is filled with the liquid to be measured. Thus, the fluid level must be at least 5 inches high to account the cumlative height of the piston. Then the lifter cylinder 108 and the piston 110 are released, allowing piston 110 to fall by force of gravity and displace fluid in bushing 106. The piston 110 moves in close proximity to measuring bushing 106 to approximate a parallel plates test for viscosity. Various embodiments of falling piston viscometers are also described in U.S. Pat. Nos. 5,959,196; 4,154,094; 3,686,931; 3,677,070; and 3,304,765, the contents of which are hereby incorporated herein by reference.

Figure 2:
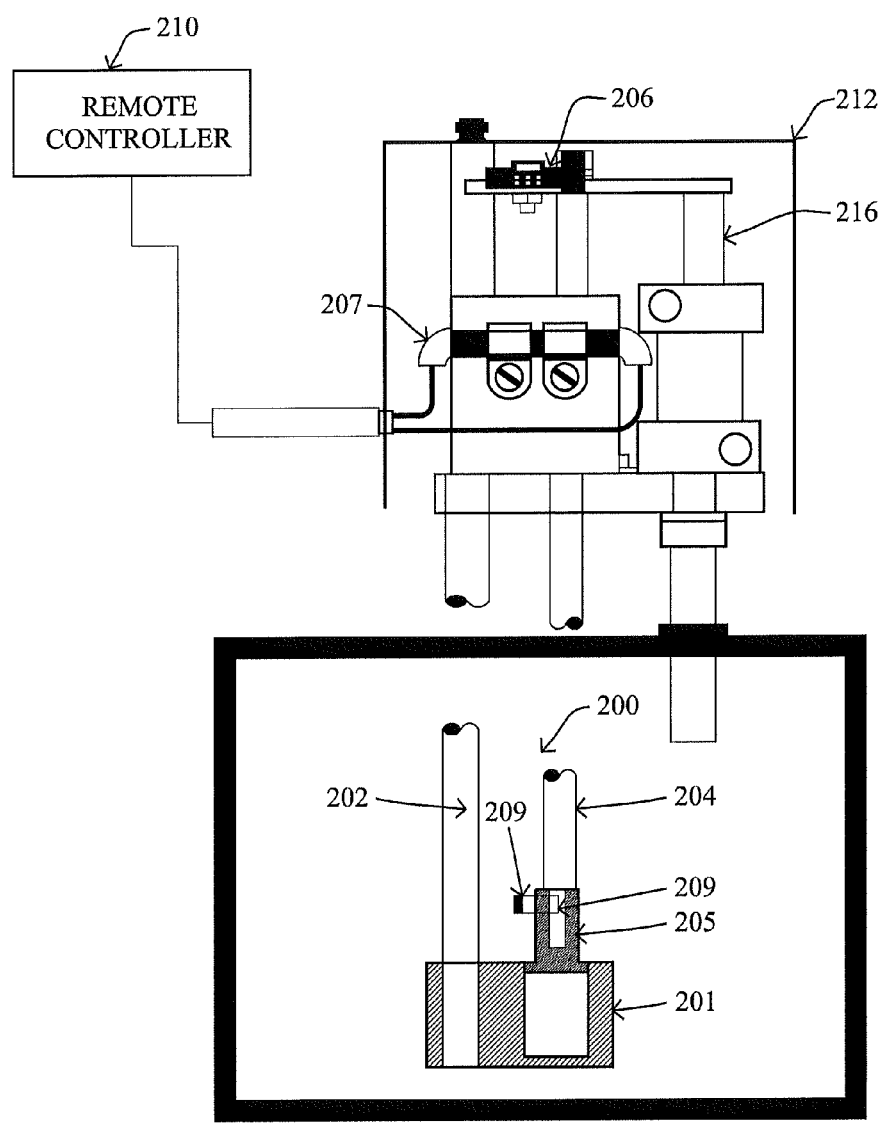
FIG. 2 is a perspective view of a system including a falling piston viscometer according to one embodiment of the invention.

FIG. 2 illustrates a viscosity control system 100 through the use of a viscometer.

Figure 3:
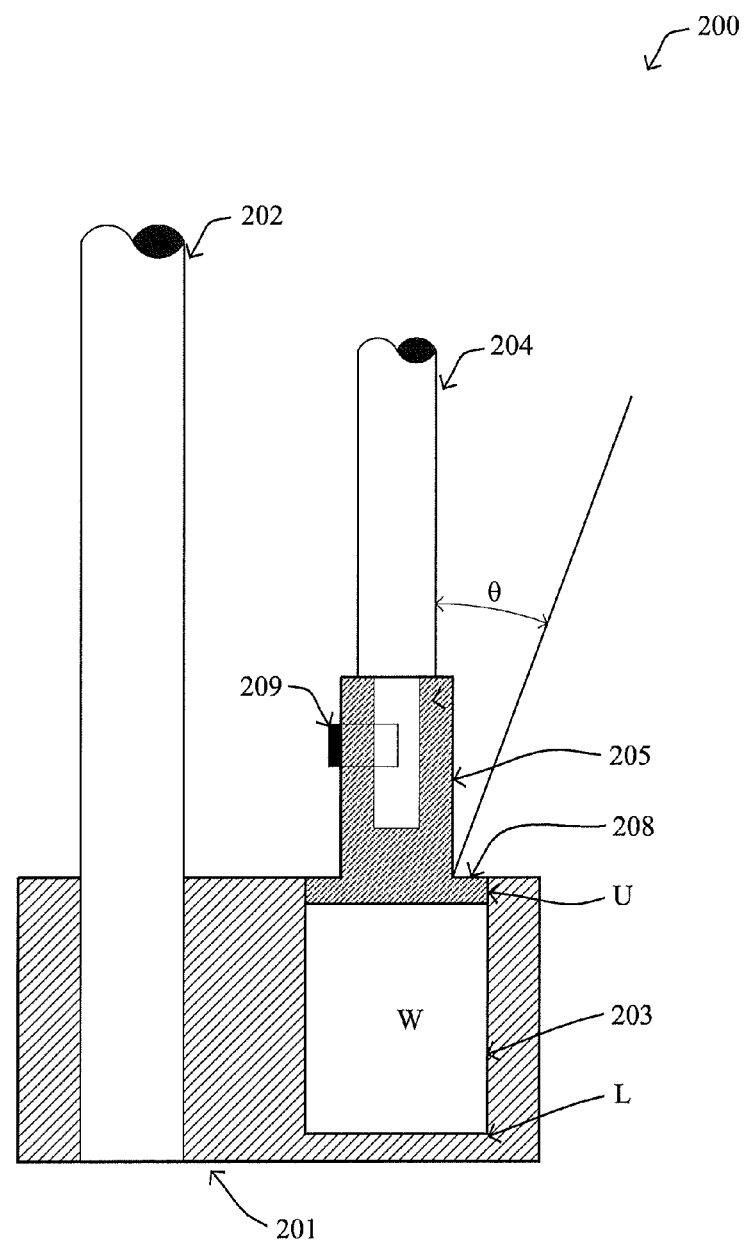
FIG. 3 is a blown up cross sectional view of the falling piston viscometer according to one embodiment of the present invention.

The viscometer in the viscosity control system 100 is a falling piston viscometer 200. More specifically, FIG. 3 shows a blown-up cross sectional view of one embodiment of the falling piston viscometer 200 according to the illustrative embodiment of the present invention. In particular, the falling piston viscometer 200 includes a measuring bushing 203 which is formed in a plate 201 with an internal depth sufficient for receiving a piston 205. The measuring bushing 203 is formed so that the piston 205 may be slidably received inside the measuring bushing 203. The measuring bushing is herein defined as a tubular shaped cylindrical depression formed to have a circumferential shape and diameter that is suitable to receive the piston 205. Fixably attached to the piston 205 is a piston rod 204 which is secured by securing mechanism 209 such as a screw or adhesive or may be integrated into the piston rod 204. By integrated it is meant that the piston 205 and the piston rod 204 can be formed as a single continuous piece or part.

The plate 201 could also functions as a support mechanism for the viscosity control system 100 as well as a receptacle for support rod 202 which is fixed within the plate 201. The plate 201 is preferably disposed perpendicular with the piston rod 201. However, the support rod 202 may also be disposed in alternative positions that would provide for adequate support of the viscosity control system 100.

The main support mechanism for the unit 200, however, in this illustrative embodiment of the present invention is support rod 202 which extends from a lower end of the unit 200 to an upper end of the unit 200 through, for example, apertures in support plates (not shown). The support 202 may be fixedly secured in the apertures via a fixing means such as a screw or a clamping device. It should be noted, however, that this is not the only means available for supporting the exemplary embodiment of the present invention and thus, this illustrative embodiment should be taken as exemplary only.

Figure 4A:
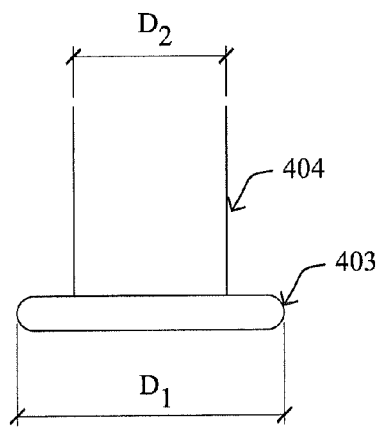
FIGS. 4A and 4B are blown up cross sectional views of alternative embodiments of the falling piston viscometer according to various embodiments of the present invention.

In the exemplary embodiment of the present invention, the piston may be embodied in cylindrical shape having a first section 403 and a second section 404. As can be seen in FIG. 4A, the first section is configured to have a diameter $D_1$ greater than that of the second section $D_2$. Preferably, however, the height of the first section is less than that of the second section. Additionally, the circumferential edges of the first section 403 of the piston 205 are modified, e.g., rounded. By modifying/rounding the circumferential edges of first section 403 of the piston, the illustrated falling piston assembly is able to provide an accurate viscosity measurement even if the piston 205 is not perfectly aligned with the measuring bushing 203. For example, by rounding the edges of the first section 403 of the piston 205, the piston 205 may be able to deviate from a central axis of the measuring bushing 203 at an angle θ, e.g., between about 0.1 degrees and about 20 degrees.

Figure 4B:
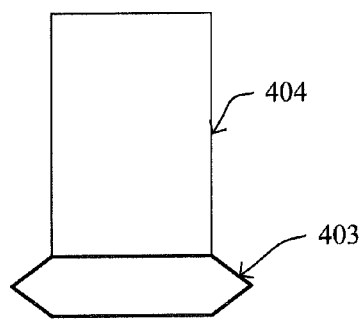

Although, the above modified circumferential edges of the first section 403 are described above as being rounded, the circumferential edges of the first section 403 of the illustrative embodiment of the present invention do not necessarily have to be rounded. Alternatively, as shown in FIG. 4B, the circumferential edges of the first section 403 of the piston 205 may be angulated so as to form a hexagonal cross sectional shape without departing from the overall goal and design of the above described invention.

In some embodiments, the first section 403 is configured such that modified circumferential edges 403 consume the entire side profile of the first section 403. Thus, the first section 403 does not have any portion having a cylindrical profile. Alternatively, the first section 403 can include a cylindrical profile between one or more modified circumferential edges.

A lifting mechanism 216, in communication with the piston 205 and piston rod 204, is configured to raise the piston 205 to an upper piston position within the measuring bushing 203, upon instruction from a remote controller 210. Upon being lifted, fluid is drawn into the measuring bushing 203 through the top and/or the bottom of the measuring bushing. The remote controller 210 through instruction to the lifting mechanism is configured to maintain the piston 205 in a raised position U for a pre-programmed time, for example, up to about 20 seconds, after which, the remote controller 210 allows the piston 205 to fall, by the force of gravity. A switch 207 mounted proximate to the piston 205 and/or piston rod 204 senses when the piston 205 reaches a lower piston position L. In particular, the time taken for the piston to travel from the upper piston position U to the lower piston position L, (typically 1 to 2 seconds), is a direct function of the viscosity of fluid received in the measuring bushing 203.

Figure 5:
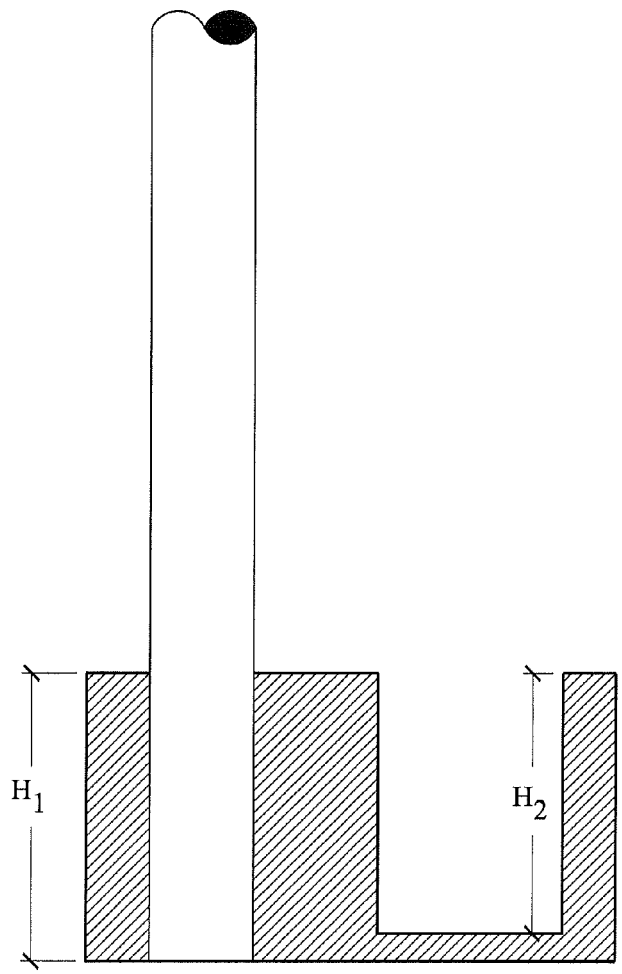
FIG. 5 is a blown up cross sectional view of the plate and measuring bushing assembly according to one embodiment of the present invention.

In some embodiments of the present invention, like the one shown in FIG. 5, the measuring bushing may be formed with a depth or height $H_2$, which in this illustrative embodiment is as about ¾ inch. Likewise, the plate 201 also may preferably be a height $H_1$, in FIG. 5, which in the illustrative embodiment of the present invention is about 1 inch. In other embodiments, however, the plate may have a height/thickness which is greater than or less than 1 inch as long as $H_1$>$H_2$ in order to accommodate the piston 205 and the measuring bushing 203 formed therein while at the same time minimizing the thickness/height of the plate in which the measuring bushing is formed. In operation, the piston 205 may be configured to be raised to an upper piston position U which is about ½ inch from the bottom of the measuring bushing 203 in order to draw fluid into the measuring bushing while at the same time allowing the piston 205 to remain in the measuring bushing.

In some embodiments of the present invention, the remote controller 210 may be configured to measure and calculate the time taken for the piston 205 to fall from the upper piston position U to the lower piston position L. Based on this measurement, the controller is able to determine the viscosity of the fluid in the measuring bushing 203. The fluid measured by the viscometer 200 may be any one of a number of fluids, however, preferably the fluid in the illustrative embodiment of the present invention is a water-based fluid or solvent-based fluid, for example, ink. However, alternative types of fluids may also be readily measured by the falling piston viscometer in the illustrative embodiments of the present invention as well.

The piston rod 204 is actuated by the lifting mechanism 216 which may be embodied as, for example, a pneumatic actuator (not shown) contained within the unit 212 which is controlled by the (external) remote controller 210. However, other means of actuation of the piston rod, such as electrical, mechanical, hydraulic, or the like are also possible.

As a means for determining when a piston has reached an upper piston position U and a lower piston position L, a switch 207 may be utilized. The switch 207 may be mounted proximate to the piston 205 and/or the piston rod 204 so that it can sense when the piston 205 reaches a lower piston position L, e.g., the bottom of the measuring bushing 203. Again, the time taken for the piston 205 to travel from the upper piston position U to the lower piston position L is a direct function of the viscosity of fluid received in the measuring bushing.

Additionally, in some embodiments of the present invention the switch 207 may be a magnetic switching mechanism. In this embodiment, the piston rod 204 would include a magnet 206 which is utilized in conjunction with a magnetic switch to detect the position of the piston 205 in the measuring bushing 203. The magnet 206 in the piston rod 204 operates the magnetic switch to measure the time it takes for the piston 205 to fall, due to the effects of gravity, through the fluid which is received in space W of the measuring bushing 203. Alternatively, in other embodiments of the present invention, the switch 207 may also be a mechanical switch or an optical sensor which is utilized to detect the position of the piston in the measuring bushing 203.

Figure 6:
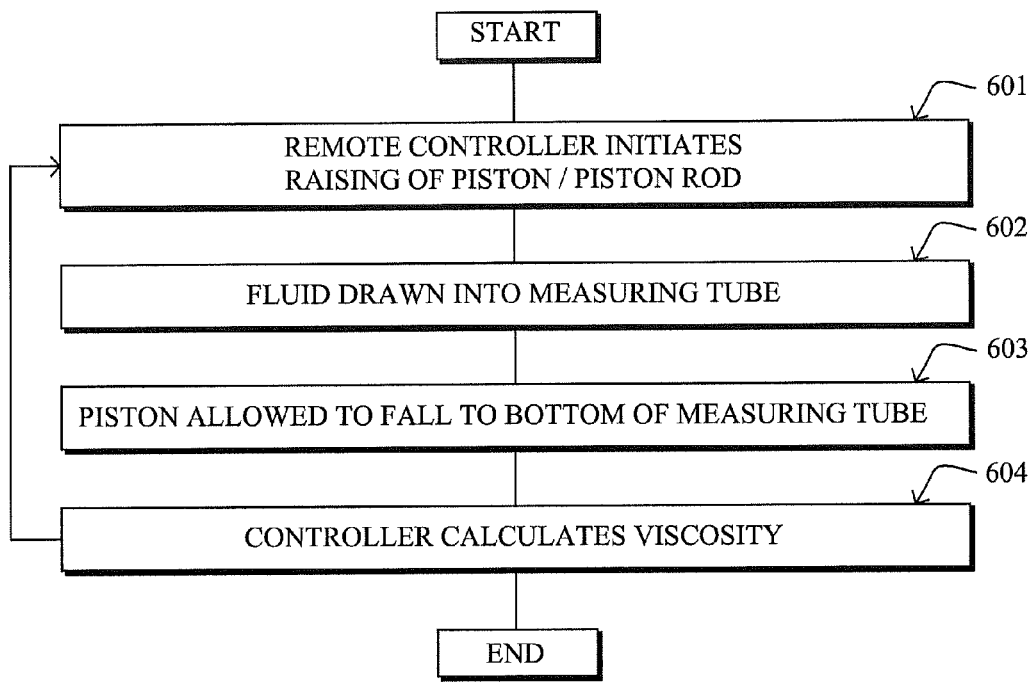
FIG. 6 is a flowchart illustrating a method for determining the viscosity of a fluid in the falling piston viscometer according to the illustrative embodiment of the present invention.

FIG. 6 is a flowchart illustrating a method for measuring the viscosity of a fluid using a measuring bushing in the falling piston viscometer of the present invention. In particular, the illustrative method begins at step 601 by issuing command instructions by the external remote controller to initiate raising of a piston to an upper piston position U in the measuring bushing from a lower piston position L in the bottom of the measuring bushing. For example, the remote controller may control an air valve which then lets air flow into an air cylinder. The air cylinder then may extend a shaft which then presses on a lift plate secured to the piston rod thereby raising the piston rod an the piston. This, however, is just one exemplary of a structure which can be used for raising the piston 205 and piston rod 204.

Then in step 602, fluid is received in the measuring bushing and after a predetermined amount of time has passed, the piston is allowed to fall back to the bottom of the measuring bushing due to the effects of gravity in step 603 until it reaches the bottom of the measuring bushing. As the piston falls, its position is sensed, by a switch, until the piston reaches a lower piston position L at the bottom of the measuring bushing.

A remote/external controller then correlates, in step 604, the time taken for the piston to travel from the upper piston position to the lower piston position with a viscosity of fluid received in the measuring bushing. Since the circumferential edges of the first section of the piston may be rounded, the angulations of the piston rod do not affect the accuracy of the measurement due to the decreased friction between the piston and the fluid (i.e. due the rounded edges). Once the viscosity of the fluid has been calculated, the process may be repeated after a predetermined amount of time has passed or until the remote controller sends instructions to restart the process.

Figure 7A:
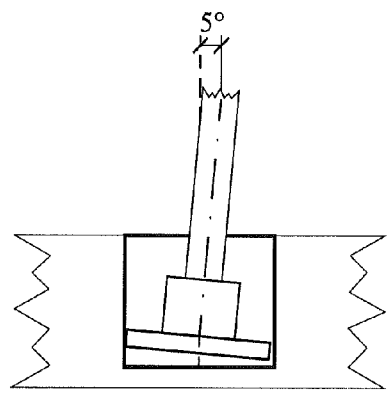
FIGS. 7A-7C are blown-up operational views of various illustrative embodiments of the present invention showing the angular advantages realized by the modified circumferential edges of the present invention.
Figure 7B:
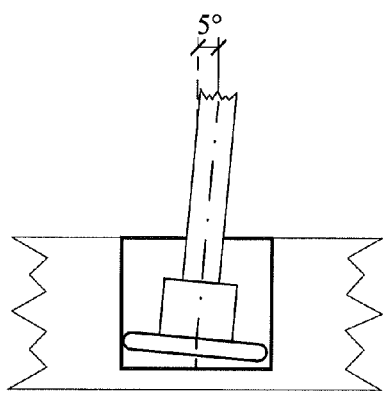
Figure 7C:
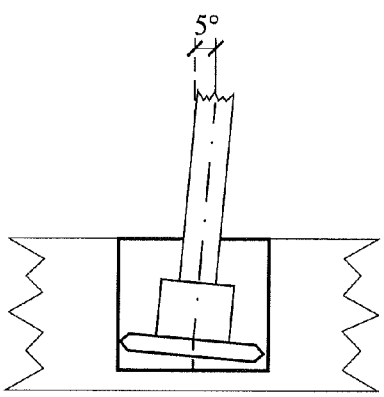

As depicted in FIGS. 7A-7C, the circumferential modified edges of the first section of the piston advantageously does not require the piston be perfectly aligned with the measuring bushing thereby allowing the piston to fluctuate/tilt angularly around the axis of the measuring bushing. As seen in FIG. 7A, a piston having circumferential edges that have not been modified will contact the walls of the measuring bushing if angled. In contrast, the piston having radiused/rounded circumferential edges in FIG. 7B and the piston having beveled circumferential edges in FIG. 7C can be angled without contacting the walls of the measuring bushing. For example, the piston may be able to deviate from a central axis of the measuring bushing at an angle between about 0.1 degrees and about 20 degrees. Thus, the manufacturer of the piston and piston rods is able to utilize cheaper more cost efficient piston rods and pistons which may be made from either lower quality metal, plastic or both. Furthermore, the overall sensitivity of the falling piston is decreased because the friction on the sides of the piston as it falls is decreased due to the modified edges of the first section as well.

The foregoing specification and the drawings forming part hereof are illustrative in nature and demonstrate certain preferred embodiments of the invention. It should be recognized and understood, however, that the description is not to be construed as limiting of the invention because many changes, modifications and variations may be made therein by those of skill in the art without departing from the essential scope, spirit or intention of the invention.

What is claimed is:

1. A viscometer comprising:
    a measuring bushing;
    a cylindrical piston slidably receivable inside the measuring bushing, the piston having a first section and a second section, wherein a circumferential edge of the first section of the piston is rounded or beveled and a bottom surface of the first section of the piston is flat, a height of the first section is less than that of the second section, and a width of the first section is greater than that of the second section;
    a lifting mechanism in communication with the piston and a piston rod, the lifting mechanism configured to raise the piston to an upper piston position, upon instruction from a controller, wherein fluid is drawn into the measuring bushing by raising the piston;
    the controller configured to maintain the piston in a raised position for a pre-programmed time, after which the controller allows the piston to fall by the force of gravity at an angle that is greater than zero; and
    a switch mounted proximate to the piston and the piston rod, wherein the switch senses when the piston reaches a lower piston position, wherein a time taken for the piston to travel from the upper piston position to the lower piston position is a direct function of the viscosity of fluid received in the measuring bushing.

2. The viscometer of claim 1, wherein the piston is not perfectly aligned with the measuring bushing.

3. The viscometer of claim 2, wherein the piston deviates from a central axis of the measuring bushing at an angle between about 0.1 degrees and about 20 degrees when the modified circumferential edge is rounded.

4. The viscometer of claim 1, wherein the upper piston position is about ½ inch from the bottom of the measuring bushing.

5. The viscometer of claim 4, wherein the measuring bushing has an internal depth of about ¾ inch.

6. The viscometer of claim 1, further comprising a remote controller configured to measure time taken for the piston to fall from the upper piston position to the lower piston position.

7. The viscometer of claim 1, wherein the measuring bushing is formed in a plate which receives the piston.

8. The viscometer of claim 7, wherein the plate is about 1 inch thick.

9. The viscometer of claim 1, wherein the fluid is selected from a group consisting of water-based fluids and solvent-based fluids.

10. The viscometer of claim 1, wherein the fluid is ink.

11. The viscometer of claim 1, wherein the fluid enters the measuring bushing from the bottom of the measuring bushing when the piston is raised by the lifting mechanism.

12. The viscometer of claim 1, the piston rod further comprises a magnet attached to the piston rod, wherein the switch is a magnetic switch and the magnet attached to the piston rod operates the magnetic switch to measure the time taken for the piston to fall through the fluid received in the measuring bushing.

13. The viscometer of claim 1, wherein the switch is a mechanical switch.

14. The viscometer of claim 1, wherein the piston, piston rod and the measuring bushing are made of metal, plastic or combination thereof.

15. The viscometer of claim 7, wherein the piston is made of plastic and the plate is made of a metal capable of receiving fluid.

16. The viscometer of claim 1, wherein the piston is made of plastic and the measuring bushing is made of metal.

17. A method for measuring the viscosity of a fluid using a measuring bushing in a viscometer, the method comprising
    initiating raising of a cylindrically shaped piston, by a controller, to an upper piston position, the upper piston position still in the measuring bushing, the piston having a first section and a second section, wherein a circumferential edge of the first section of the piston is rounded or beveled and a bottom surface of the first section of the piston is flat, a height of the first section is less than that of the second section, and a width of the first section is greater than that of the second section;
    receiving fluid in the measuring bushing;
    allowing the piston to fall to a lower piston position at an angle that is greater than zero;
    sensing, by a switch, when the piston reaches the lower piston position; and
    correlating a time taken for the piston to travel from the upper piston position to the lower piston position with a viscosity of the fluid received in the measuring bushing.

18. A viscometer comprising:
    a measuring bushing within a plate disposed beneath a piston assembly;
    a cylindrically shaped piston slidably receivable inside the measuring bushing, the piston having a first section and a second section, wherein a circumferential edge of the first section of the piston is rounded or beveled and a bottom surface of the first section of the piston is flat, a height of the first section is less than that of the second section, and a width of the first section is greater than that of the second section;

a piston rod in communication with the piston, wherein the piston rod is not perfectly straight;

a magnet embodied in the piston rod;

a lifting mechanism in communication with the piston rod and piston, the lifting mechanism configured to raise the piston to an upper piston position, and allow fluid to enter the measuring bushing once the piston rod has been raised;

a magnetic switch mounted proximate to the piston and piston rod, wherein the magnet switch senses when the piston reaches a lower piston position, wherein a time taken for the piston to travel from the upper piston position to the lower piston position is a direct function of the viscosity of the fluid received in the measuring bushing; and at least one controller configured to operate the lifting mechanism, the piston rod, and the switch so as to determine the viscosity of the fluid while still allowing the piston to fall in the fluid at an angle that is greater than zero.

* * * * *